US012635891B2

(12) United States Patent
Castagna et al.

(10) Patent No.: US 12,635,891 B2
(45) Date of Patent: May 26, 2026

(54) PROCESS AND SYSTEM FOR COLLECTING, STORING, ANALYZING AND VISUALIZING ELECTROCARDIOGRAPHIC DATA (ECG) IN REAL TIME

(71) Applicant: LÓTUS MEDICINA AVANÇADA, Belo Horizonte (BR)

(72) Inventors: Marco Tulio Vilaca Castagna, Brumadinho (BR); Ilene Maria Guimaraes de Siqueira Castagna, Brumadinho (BR)

(73) Assignee: Lótus Medicina Avançada, Horizonte (BR)

( * ) Notice: Subject to any disclaimer, the term of this patent is extended or adjusted under 35 U.S.C. 154(b) by 316 days.

(21) Appl. No.: 18/474,713

(22) Filed: Sep. 26, 2023

(65) Prior Publication Data
US 2024/0016395 A1 Jan. 18, 2024

Related U.S. Application Data

(63) Continuation-in-part of application No. 16/347,777, filed as application No. PCT/BR2017/050219 on Aug. 3, 2017, now Pat. No. 11,806,160.

(30) Foreign Application Priority Data

Nov. 7, 2016 (BR) .......................... 102016025939-8

(51) Int. Cl.
*A61B 5/0205* (2006.01)
*A61B 5/00* (2006.01)

(52) U.S. Cl.
CPC .......... *A61B 5/0205* (2013.01); *A61B 5/0022* (2013.01); *A61B 5/6804* (2013.01);
(Continued)

(58) Field of Classification Search
CPC ... A61B 5/0205; A61B 5/0022; A61B 5/6804; A61B 5/6823; A61B 5/6898;
(Continued)

(56) References Cited

U.S. PATENT DOCUMENTS

| | | | |
|---|---|---|---|
| 4,288,006 | A | 9/1981 | Clover, Jr. |
| 6,304,797 | B1 | 10/2001 | Shusterman |

(Continued)

FOREIGN PATENT DOCUMENTS

| | | | |
|---|---|---|---|
| BR | 132021018370-4 E2 | 12/2022 | |
| CN | 102940488 A | 2/2013 | |

(Continued)

OTHER PUBLICATIONS

Hsu et al., "Design of a Wearable 12-Lead Noncontact Electrocardiogram Monitoring System", Sensors, Mar. 28, 2019 (13 pages).
(Continued)

*Primary Examiner* — Linda C Dvorak
*Assistant Examiner* — Abigail Bock
(74) *Attorney, Agent, or Firm* — Merchant & Gould P.C.

(57) ABSTRACT

The present application refers to a process and a system for collecting, storing, analyzing and visualizing electrocardiographic (ECG) data collected by portable ECG device (100) with embedded wireless communication technology, additionally containing a portable ECG device (100), a hermetically sealed box (200) of medicines containing a lock system comprising a lock (220), a first device (310) to be accessed by the patient, a second device (320) to be accessed by the medical professional, a platform for graphical display of ECG data, and a remote data storage and processing central. The hardware board of the portable ECG device contains wireless communication technology, global positioning system (GPS), start button (141), rechargeable battery charging port, and an equipment configuration and programming port.

(Continued)

The battery (120) is Li-Ion type, containing LEDs indicating device operation, and waiting for connection. The battery status is displayed on the app display. In one embodiment, an electrode (130B) is positioned on the bottom cover (110B) of the housing (110A, 110B, 110C) of the ECG device (100).

13 Claims, 8 Drawing Sheets

(52) U.S. Cl.
CPC .......... *A61B 5/6823* (2013.01); *A61B 5/6898* (2013.01); *A61B 5/7225* (2013.01); *A61B 5/7271* (2013.01); *A61B 5/747* (2013.01); *A61B 2505/01* (2013.01); *A61B 2560/02* (2013.01); *A61B 2560/0406* (2013.01); *A61B 2560/0431* (2013.01); *A61B 2560/0468* (2013.01); *A61B 2562/0204* (2013.01); *A61B 2562/043* (2013.01); *A61B 2562/164* (2013.01); *A61B 2562/221* (2013.01)

(58) Field of Classification Search
CPC ..... A61B 5/7225; A61B 5/7271; A61B 5/747; A61B 2505/01; A61B 2560/02; A61B 2560/0406; A61B 2560/0431; A61B 2560/0468; A61B 2562/0204; A61B 2562/043; A61B 2562/164; A61B 2562/221

See application file for complete search history.

(56) References Cited

U.S. PATENT DOCUMENTS

| | | | |
|---|---|---|---|
| 6,970,731 | B1 | 11/2005 | Jayaraman et al. |
| 7,412,281 | B2 | 8/2008 | Shen et al. |
| 9,282,893 | B2 | 3/2016 | Longinotti-Buitoni |
| 9,569,588 | B2 | 2/2017 | Lowe |
| 9,569,592 | B2 | 2/2017 | Heffron |
| 9,662,030 | B2 | 5/2017 | Thng |
| 10,123,741 | B2 | 11/2018 | Wang et al. |
| 2007/0219454 | A1 | 9/2007 | Guzzetta et al. |
| 2012/0158074 | A1 | 6/2012 | Hall |
| 2013/0254966 | A1 | 10/2013 | Pattison |
| 2013/0281815 | A1 | 10/2013 | Varadan |
| 2014/0070957 | A1 | 3/2014 | Longinotti-Buitoni |
| 2014/0278475 | A1 | 9/2014 | Tran |
| 2014/0364779 | A1 | 12/2014 | Oestreich |
| 2015/0272464 | A1 | 10/2015 | Armoundas et al. |
| 2016/0066809 | A1 | 3/2016 | Chebiyyam |
| 2016/0095527 | A1 | 4/2016 | Thng et al. |
| 2016/0287480 | A1 | 10/2016 | Hancock et al. |

FOREIGN PATENT DOCUMENTS

| | | | |
|---|---|---|---|
| KR | 2009-0123963 | A | 12/2009 |
| KR | 2010-0126107 | A | 12/2010 |
| WO | 8902246 | A1 | 3/1989 |
| WO | 2005/034743 | A1 | 6/2006 |
| WO | 2008/116822 | A2 | 10/2008 |
| WO | 2012088398 | A2 | 6/2012 |
| WO | 2015/179015 | A1 | 11/2015 |

OTHER PUBLICATIONS

Shao et al., "A Wearable Electrocardiogram Telemonitoring System for Atrial Fibrillation Detection", Sensors, Jan. 22, 2020 (16 pages).

Geng Yang et al., "A Health-IoT Platform Based on the Integration of Intelligent Packaging, Unobtrusive Bio-Sensor and Intelligent Medicine Box", IEEE Transactions on Industrial Informatics, pp. 2180-2191, Nov. 2014.

Upkar Varshney, "Wireless Medication Management System: Design and Performance Evaluation", Department of Computer Information Systems Georgia State University, 2011 (8 pages).

200

200

210

PROCESS AND SYSTEM FOR COLLECTING, STORING, ANALYZING AND VISUALIZING ELECTROCARDIOGRAPHIC DATA (ECG) IN REAL TIME

FIELD OF INVENTION

The present invention is part of the field of medical applications aimed at monitoring patients with high cardiovascular risk, with the possibility of diagnosis as early as possible, aiming to shorten the time for the definitive treatment of those who have acute coronary syndrome (ACS), acute infarction myocardial infarction (AMI), cardiac arrhythmias such as acute atrial fibrillation (AAF) and other cardiac arrhythmias or other cardiac pathologies detectable by electrocardiographic tracing analysis of large amounts of big data analytics data and deep learning with the use of artificial intelligence, using the internet of things, as well as for recreational and/or sports applications aimed at monitoring individuals who wish to have their electrocardiographic tracing monitored during recreational or sporting physical activity, with the possibility of evaluating their performance separately or progressively or even having their electrocardiogram registered and recorded for 24 hours or more (Holter type).

DESCRIPTION OF THE STATE OF ART

Some documents were found that present technologies on garments with ECG or GSM or GPS or Bluetooth technology coupled, however, such technologies lack the specified functionality of using a complex monitoring system integrated with the patient, as well as access to the airtight plastic box containing drugs for emergency care with remote opening through encrypted digital signature of a medical specialist.

Document US20160066809 describes a garment with markings for positioning and fixing electrodes. The garment is composed of horizontal and vertical embroideries, crossing each other, of stainless-steel thread on the fabric of the garment, alone or associated with paint or conducting pastes or extensible conductive fabrics in carbon or silver. It makes no reference to any device that contains a hermetic reservoir for medications that allow remote dispensing of medications in the case of specific needs such as ACS, AMI, FAA and other cardiac arrhythmias, to initiate early treatment of these pathologies.

Document US201302818150 consists of an electrophysiological monitoring system, which records ECG data that is attached to a garment. It presents a controller and a wireless transmitter to a receiver configured to collect data generated by the ECG and, in case of any abnormality, issue an alert. Document WO2012088398 describes a garment comprised by an array of interconnected sensors, without showing that these sensors are part of an ECG device for intermittent or continuous monitoring. Such documents do not describe the real-time ECG remote monitoring functionality, nor do they refer to a device that contains a hermetic reservoir for drugs that allow remote dispensing of drug doses.

Document US20070219454 describes a method for indicating heart disease through electrocardiogram signals from a lead set fixed on the body of a patient for detecting and mapping heart diseases in an individual, and document U.S. Pat. No. 7,412,281 refers to a system of wireless electrocardiogram monitoring for long-term fitness monitoring. None of these documents refer to a technology with complex functionalities for mapping and transmitting remote data to a monitoring center, as well as access to heart disease treatment, issuing reports through AI or real-time monitoring by a practitioner. Additionally, such documents do not present an airtight box containing medication.

Documents EP1673010 and WO8902246 describe a vest that is adapted to be used over the torso of a patient, and an ambulatory evaluation system for monitoring the cardiac activity of a patient, however without containing the complete integrated monitoring system, intermittent and remote reading of patient data with the possibility of immediate treatment and emergency care.

Document Design of a Wearable 12-Lead Noncontact Electrocardiogram Monitoring System (https://doi.org/10.3390/s19071509) presents a wearable system with virtual monitoring of electrocardiographic data obtained through sensors positioned on the garment. The system has wireless data transmission technology and exclusively mentions the use of 12-lead ECG, without allowing the reduction in the number of electrodes. The document A Wearable Electrocardiogram Telemonitoring System for Atrial Fibrillation Detection (https://doi.org/10.3390/s20030606), in turn, presents a communication system through the internet of things between the patient and the professional in the field. The main factors covered by the present invention are not presented, such as the issuance of a report via AI, the connection to smart devices, the presence of a medicine box with remote release of medicine dose and an emergency notification.

None of the documents found in the state of the art mention or allude to similar technology or technologies that present performance, efficiency and integration of equipment similar to those of the present invention, as well as complex functionalities of mapping and remote data transmission to a monitoring center, use of artificial intelligence, "deep learning" and big data analytics, as well as access to early initiation of treatment for coronary artery disease, whether AMI, ACS or AAF with less than 48 hours of start date or other cardiac arrhythmias, when applicable, by opening the hermetic plastic box containing medications as described above, by remote transmission of an electronic signal, authorized and carried out by the practitioner who performed the ECG.

The Applicant has conceived, tested, and incorporated the present invention in order to overcome the deficiencies of the state of the art and obtain the purposes and advantages abovementioned and explained below.

SUMMARY OF THE INVENTION

The present invention is presented and characterized in the independent claims, while the dependent claims describe other characteristics of the invention or modalities related to the main inventive idea.

The present invention provides a process for collecting, storing, analyzing, and visualizing electrocardiographic (ECG) data collected by a portable ECG device with embedded wireless communication technology, additionally containing at least one device with wireless communication technology, an airtight box containing medicines, and at least one central data storage system. Additionally, the process includes the use of a portable ECG device, a hermetically sealed medicine box containing an electronically operated locking system and a manually operated safety lock, a first device to be accessed by the patient, a second device to be accessed by the practitioner, a platform for graphical display of ECG data, and a central for remote data storage and processing.

The ECG device reads electrocardiographic data, through an array of N electrodes attached to a mini portable ECG device and transmits them to the platform through wireless communication technology, embedded in a hardware board. The electrode array N can be formed by 4 electrodes. The hardware board and the mini-ECG device are contained in a housing, which additionally comprises a rechargeable battery. The hardware board contains, in addition to wireless communication technology, global positioning system (GPS), start button (Start), rechargeable battery charging port and equipment configuration and programming port. In some embodiments of the present invention, the battery is of the Li-Ion type, containing LEDs that serve as light indicators of operation and battery status. The battery level of the ECG device is displayed on the display of the application, ranging from 0% to 100%.

The device of this invention has a connection to wireless devices, via bluetooth or other wireless means, that is, gadgets like smart rings, smart bracelet, smart watch, smart oximeter, abdominal and chest strap with smart sensors, smart stethoscope for audio capture, to remotely auscultation of biological sounds, probes with ultrasound sensor and intelligent Doppler, all for capturing signals for monitoring biological, cardiac, pulmonary and abdominal parameters, including ultrasound images of the abdomen and heart, continuous arterial hypertension for 24 hours by remote pulse plethysmography, in addition to assessing heart valve pathologies also by plethysmography, expansion, lung rate and compliance, endocrine and metabolic parameters, among others, which are wirelessly connected to the digital platform via smartphones.

The process according to the present invention collects the electrocardiographic data and transmits them to the platform, through Wi-Fi, BLE (Bluetooth), GSM technology, 3G, 4G, 5G and, optionally, through data transmission cable. The signals captured by the ECG device are treated by a data analysis suite that performs cleaning, amplification, and processing of the signal. Signal processing is carried out by algorithm-numerical modeling, which can be LSTM (Long Short-Term Network), UTC (Universal Transformation Coefficient), any vectorized formulation (vector-Based) or another algorithm-numerical method used in the state of art, being the calculations performed compared to the 12-lead ECG reading, based on the 3-lead reading with 4 electrodes, which can reach 15, 18 or even 22 leads, taking into account that there may be variations when compared to the traditional 12-lead ECG leads with 10 electrodes. In one embodiment, the analysis suite is a hardware embedded on the hardware board and is composed of at least one signal amplifier, at least one high-pass filter, and at least one microprocessor, and the numerical method is chosen automatically based on the number of input ports in use (number of electrodes). In one embodiment, the analysis suite is a software embedded in the first device and is an integral part of the platform software for graphically displaying the ECG, performing the functions of high-pass filter, signal amplifier and processing, and the numerical method is chosen automatically, based on the number of data read and transmitted (number of electrodes). If 4 data are read or 4 input ports are used, the algorithm-numerical method reproduces the M additional signals, being M=8, for 12-lead analysis, and M=18, for 22-lead analysis.

Data is stored on the platform, which can be an application installed on the device (App) or an application installed in the data central and accessible via the Web (Web App). The platform may alternatively be accessible via the Web.

The reading process begins with the attachment of the N electrodes to the patient in which the data will be read, the electrodes being fixed directly on the skin or attached to a vest-type garment. After fixation, the ECG device is started by the start button, the electrocardiographic data are collected and processed, and the geospatial positioning of the patient is collected. Electrocardiographic data and patient positioning information are forwarded to the first device in real time, via Wi-Fi, BLE, GSM, 3G, 4G, 5G or data transmission cable. Data is received by the first device for storage, display and analysis by the platform accessed by the first device. Finally, the treated and processed data are conveyed to the central for remote data storage and processing through at least one of Wi-Fi, 3G, 4G, 5G, LAN, Ethernet, and other network connections. If the analysis suite is a hardware, the electrocardiographic data are received already treated and processed by the first device, and they are only stored for later display and analysis by the platform. If the analysis suite is a software, the electrocardiographic data are received by the first device and are processed before storage for later display and analysis. Electrocardiographic tracings can be stored for a long period of 24 hours or more, characterizing the Holter embodiment with 12 leads, based on the reading of 3 leads with 4 electrodes, which can reach 18 or even 22 leads, considering that there may be variations when compared to the traditional 12-lead ECG with electrodes.

In an embodiment, activation of the start button is performed manually by the patient, pressing a physical button on the ECG device. In an embodiment, the activation of the start button (Start) is done remotely, through the indication of the beginning of the reading carried out by the platform, by pressing a virtual button. Remote activation can be performed by the patient himself through the first device by sending an activation signal from the first device start button to the ECG device via at least one of BLE, Wi-Fi, 3G, 4G and 5G technologies. Alternatively, remote activation may be performed by the medical professional using the second device, through the steps of sending the activation signal from the start button of the second device to the central for remote data storage and processing via at least one of Wi-Fi, 3G, 4G, 5G, LAN, Ethernet and other network connections, issuing a signal to activate the start button of the central for remote data storage and processing to the first device through at least one of Wi-Fi, 3G, 4G, 5G, LAN, Ethernet and other network connections, and sending a start button activation signal from the first device to the ECG device via at least one of BLE, Wi-Fi, 3G, 4G and 5G technologies.

Electrocardiographic data and geospatial positioning data are received by the central for remote data storage and processing in real time for analysis of the processed ECG data, in which the analysis considers the ECG data history of the patient that already exists in the storage and processing central and the history of publicly known ECG data, the publicly known history being part of the database of the storage and processing central, and the publicly known history including ECG data of heart diseases, such as valve heart disease, hypertensive heart disease, heart disease stroke, acute coronary syndromes, acute myocardial infarction, congenital heart disease, myocardial diseases, and ECG data of arrhythmias of the heart, such as tachycardia, bradycardia, sinus node disease, atrial fibrillation, extrasystoles, fascicular block, atrioventricular block, ventricular arrhythmia, hereditary arrhythmia and sudden death. In an embodiment, data is accessed by the practitioner in real time for analysis and report issuance. Diagnosis is selected by the professional in their application according to the interpretation of the ECG tracing and the symptoms presented by the patient and selected in the application from a list of typical symptoms of cardiac pathologies. After analysis, the practitioner sends the report to the patient through an application notification, which is transmitted in real time to the application of the patient.

In one embodiment, the analysis is performed by artificial intelligence, in the data storage central, in which the analysis classifies in real time the ECG data received in N, A or G, and the data classified as N (Normal) indicate absence of heart disease or arrhythmia, the data classified as A (Altered) indicate the existence of heart disease or arrhythmia without imminent risk of death or patient disability, and the data classified as G (Severe) indicate the existence of imminent risk of death or patient disability. The diagnosis is selected by comparing the ECG tracing and the symptoms presented by the patient, selected in the application from a list of typical symptoms of cardiac pathologies, with existing data in the database. After analysis, the data storage central sends the practitioner and/or the patient a notification regarding the condition presented by the patient. Notification is either app notification or push notification type.

In one embodiment, the data classified as A is forwarded to the practitioner and stored in the system, and a notification is forwarded to both the practitioner and the patient, and the practitioner remotely releases the lock of the hermetically closed box locking system so that the patient have access to the medication dosage released by the professional.

In a embodiment, the patient releases the medication box manually, by actuating the safety lock.

In one embodiment, data classified as "G" are forwarded to the practitioner and stored in the system, and an urgent notification is forwarded to both the practitioner and the patient, and the notification contains at least the geospatial location of the patient and the heart disease or identified anomaly. An emergency medical center selected by the geospatial location of the patient is contacted automatically. An emergency notification is forwarded to at least one emergency contact pre-registered by the patient, and the emergency notification contains at least the geospatial location of the patient and the contact of the emergency medical center contacted. The practitioner remotely releases the locking system of the hermetically closed box so that the patient has access to the medication dosage released by the practitioner and specific to the clinical condition of the patient, after the evaluation of the ECG tracing by the practitioner and corroboration of the report.

The present invention additionally provides a system for collecting, storing, analyzing, and visualizing electrocardiographic data (ECG) collected by a portable ECG device with embedded wireless communication technology, additionally containing at least one device with wireless communication technology, an airtight box containing medication and at least one central data storage system. Additionally, the system includes a portable ECG device, a hermetically sealed medicine box containing a locking system, a first device to be accessed by the patient, a second device to be accessed by the practitioner, a platform for graphical display of ECG data and a central for remote data storage and processing.

The ECG device performs the reading of electrocardiographic data, through an array of 4 electrodes coupled to a mini portable ECG device and transmits them to the platform through wireless communication technology, embedded in a hardware board. The hardware board and the mini-ECG device are contained in a housing, which additionally comprises a rechargeable battery. The hardware board contains, in addition to wireless communication technology, global positioning system (GPS), start button (Start), rechargeable battery charging port and equipment configuration and programming port. In some embodiments of the present invention, the battery is of the Li-Ion type, and it contains LEDs acting as light indicators of operation and battery status. The status or battery level of the ECG device is shown on the app display of the patient.

In one embodiment, the electrode array connects to the ECG device through a conductive path. In one embodiment, the electrode assembly sends the collected data to the ECG device via wireless transmission.

In one embodiment, the electrode array is positioned directly on the skin of the patient. In one embodiment, the electrode array is attached to a garment worn on the chest region of a patient, wherein the garment is composed of woven textile yarns of any one of polyamide, synthetic rubber, expandable fiber, natural fibers and synthetic fibers and has in its manufacturing composition a set of stainless steel wires arranged in any shape between horizontal, vertical, diagonal, in square mesh, in rectangular mesh and any combination of horizontal, vertical and diagonal configuration. Additionally, the garment has antibacterial treatment. In one embodiment, the garment is biodegradable. In one embodiment, the set of steel wires has conductivity properties of electronic signals. In one embodiment, the set of steel wires is coated with one of conductive material pastes and conductive material inks, the conductive material being any of carbon and silver.

The ECG device housing comprises a top cover, a bottom cover, and an intermediate cover, and in one embodiment, an electrode of the electrode array is attached to the bottom cover of the portable ECG device. The housing is sealed from water ingress and/or is immersion-proof. In one embodiment, the enclosure has width L, with L being between 20 mm and 40 mm, height H, with H being between 8 mm and 25 mm, and length C, with C being between 40 mm and 70 mm The ECG device sends a first notification to the first device if the rechargeable Li-Ion battery reaches 20% charge. In addition, the ECG device sends frequent notifications of battery status and recharge request, with weekly frequency for battery greater than 20% and daily frequency for battery status equal to or less than 20%. In one embodiment, the ECG device initiates low power mode if the Li-Ion battery reaches 20% charge.

According to an embodiment of the present invention, a notification is sent to the second device, accessed by the practitioner, for cases of patients with heart diseases or pre-diagnostic cardiac anomalies, in which the notification informs the remaining charge level in the Li-Ion battery, the last ECG reading and the last geospatial location of the patient.

According to an embodiment of the present invention, the ECG device is attachable to portable devices with wireless technology, by means of any one of BLE and NFC, in which the wireless portable devices are any of smart ring, smart band and smart watch.

According to an embodiment of the present invention, the platform for graphical display of ECG data additionally has the functions of reading, processing, and displaying vital signs among oxygen saturation, heart rate, pulse rate, blood pressure, body temperature, vascular auscultation and respiratory auscultation, ultrasound data, and Doppler ultrasound data. Cardiac and pulmonary (respiratory) auscultations are performed using a stethoscope adapted for connection to the first device, having any connection port between USB type A, USB type B, USB type C, USB mini type A, USB mini type B, micro-USB type A, micro USB type B, USB 3.0 and lightning. Oxygen saturation is determined using at least one of pulse oximetry and finger or wristband oximetry steps. Ultrasound data and Doppler ultrasound data are collected through a mini ultrasound adapted to the connection with the first device, having any connection input between USB Type A, USB Type B, USB Type C, USB mini type A, USB mini-Type B, micro USB Type A, micro USB Type B, USB 3.0 and lightning.

OBJECTIVES OF THE INVENTION

One objective of the present invention is to provide a portable ECG device, easy to use and handle, for reading and processing electrocardiographic data in real time and enabling preventive action to be taken in the event of a cardiovascular event.

Another objective of the present invention is to provide a portable ECG device capable of long-term electrocardiographic recording, with continuous use for 24 hours or more than 24 hours, Holter mode, based on the reading of 3 leads with 4 electrodes, which can reach 15, 18 or even 22 leads, taking into account that there may be variations when compared to the traditional 12-lead ECG with 10 electrodes.

Another objective of the present invention is to present an electrocardiographic data reading process, as well as the processing, analysis, display and cloud storage steps, accessible through a platform by both the patient and the practitioner. The integrated technology present in this invention meets the needs of athletes and sportsmen who aim at the periodic evaluation and control of cardiovascular functioning. Additionally, the technology of the present invention provides the possibility of real-time medical assistance in cases of cardiovascular events through online monitoring by the practitioner, with the release of an appropriate drug dose for the specific clinical situation of the patient or user. Additionally, the technology of the present invention allows the quick location and prompt care of patients at serious cardiovascular risk that may cause momentary or permanent incapacitation. Additionally, the technology of the present invention allows the user to perform periodic control of electrocardiographic data during daily activities without the need to use large or uncomfortable equipment, allowing the easy performance of exams, such as Holter and Map, the maintenance of the cardiovascular history of the user and the visualization, in real time, of the read and processed data.

It is another objective of the present invention to provide a system that can be integrated with wireless technologies, such as smart rings, smart bracelets, smart watches, among others, in addition to allowing quick access to electrocardiographic data stored on the platform.

It is another objective of the present invention to provide a system and a process for collecting and analyzing electrocardiographic data that allows the diagnosis of cardiovascular events remotely, with real-time monitoring by a practitioner, with the issuance of medical reports, application of the correct dose medication and assistance in case of emergency.

BRIEF DESCRIPTION OF THE FIGURES

These and other features of the present invention will become evident from the following description of some embodiments, given as a non-restrictive example with reference to the accompanying drawings, in which.

For ease of understanding, the same reference numbers have been used, where possible, to identify identical common elements in the drawings. It is understood that elements and characteristics of an embodiment can be conveniently incorporated in other embodiments without further clarification.

DETAILED DESCRIPTION OF THE INVENTION

Figure 1A:
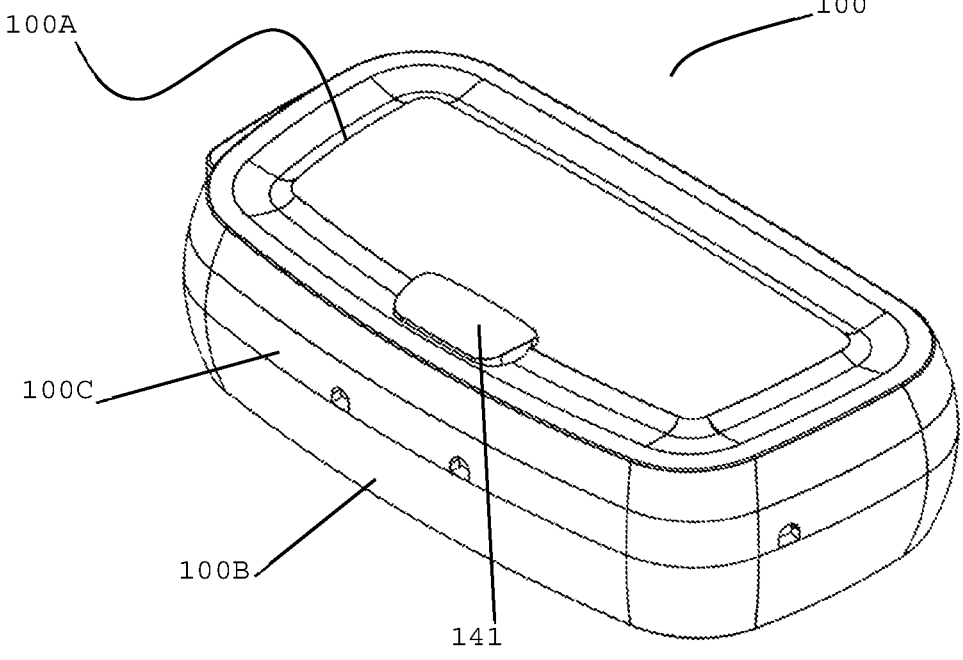
FIGS. 1A and 1B show perspective views of different embodiments of the ECG device of the present invention.
Figure 1B:
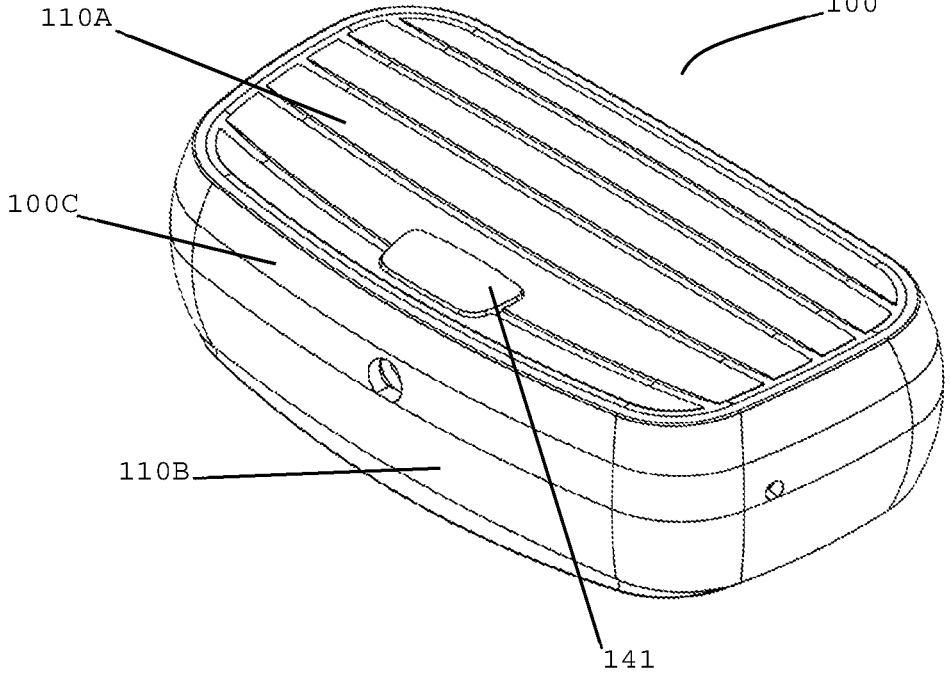
Figure 2:
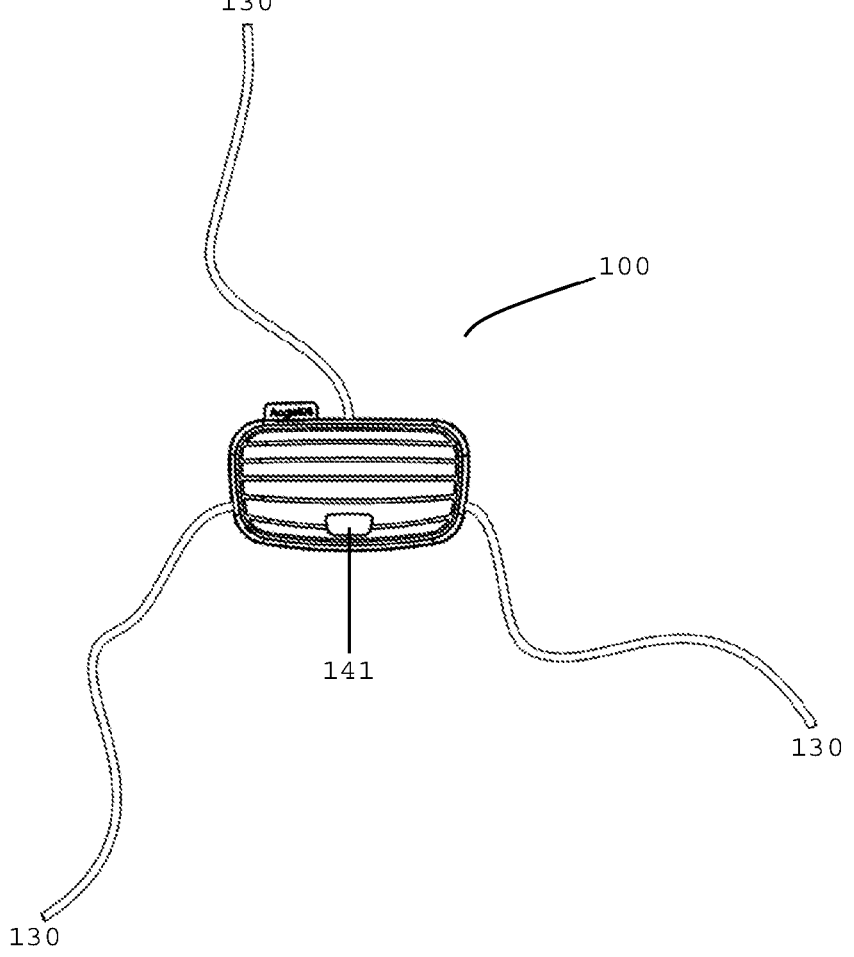
FIG. 2 shows an embodiment of the ECG device of the present invention, with electrode connection outputs.
Figure 3:
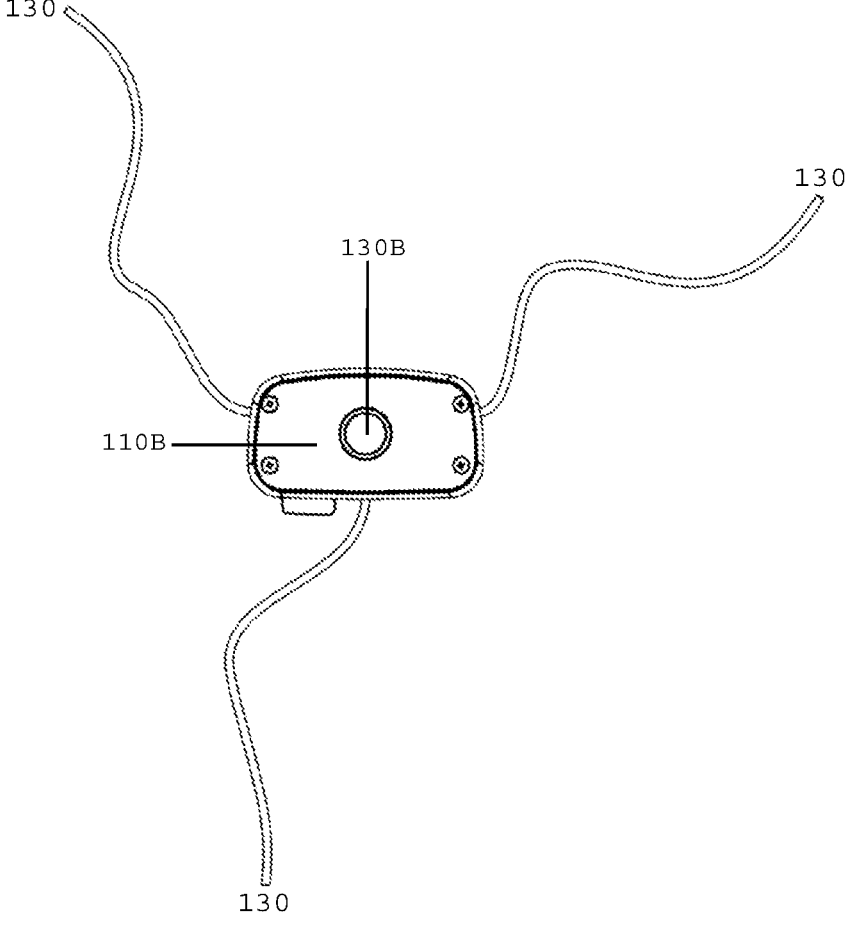
FIG. 3 shows the bottom view of the embodiment contained in FIG. 2, in which the presence of an electrode on the bottom cover of the housing is highlighted.
Figure 4:
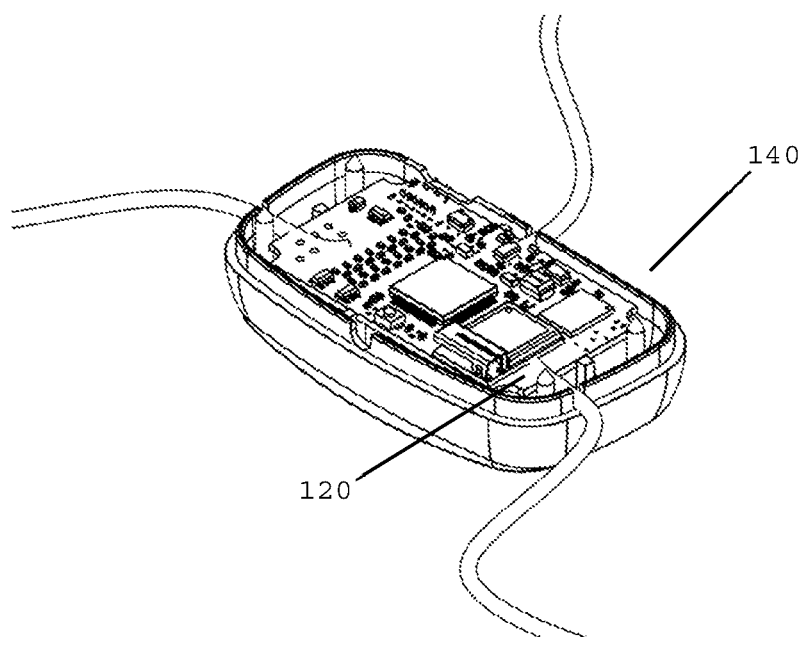
FIG. 4 shows an inside view of the ECG device housing of the present invention.
Figure 5:
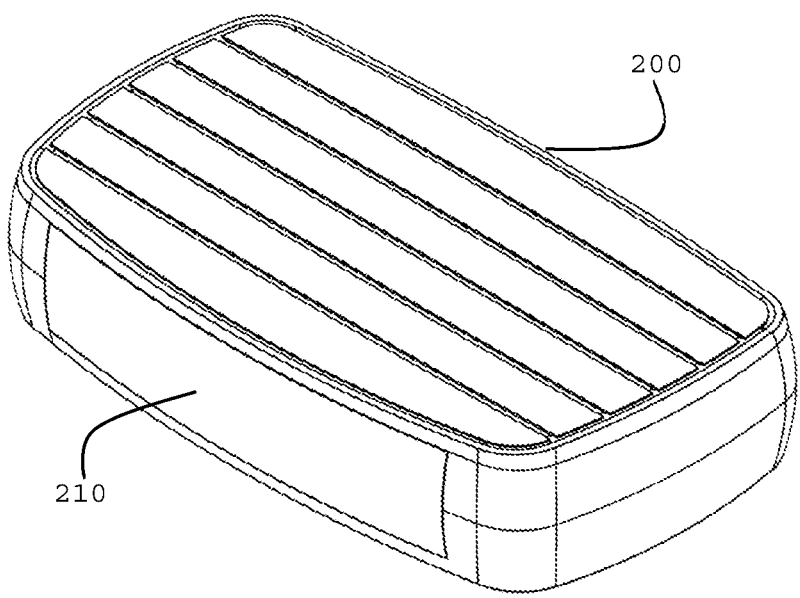
FIG. 5 shows the perspective view of an embodiment of the airtight medicine box.
Figure 6A:
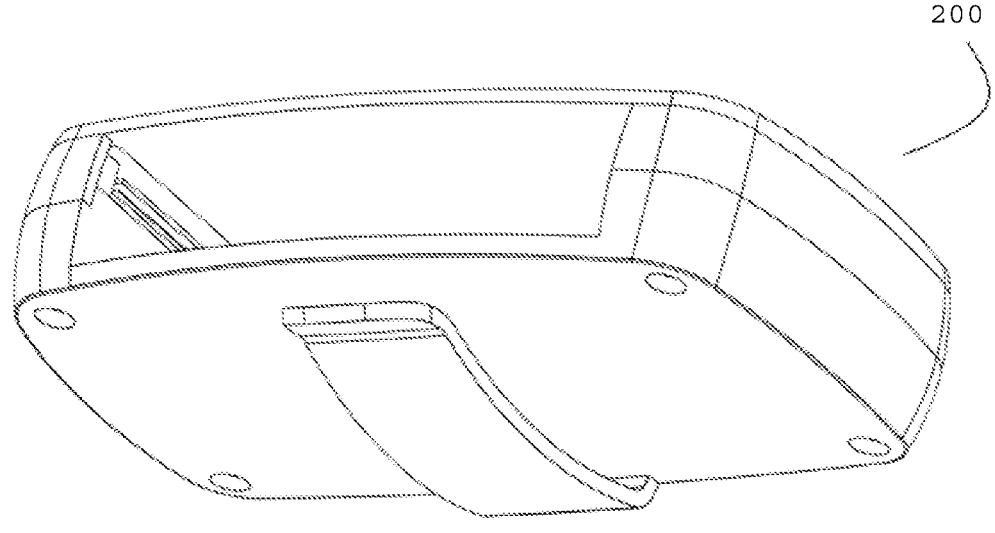
FIG. 6A shows a perspective view of an embodiment of the airtight medicine box without the inclusion of the medicine drawer.
Figure 6B:
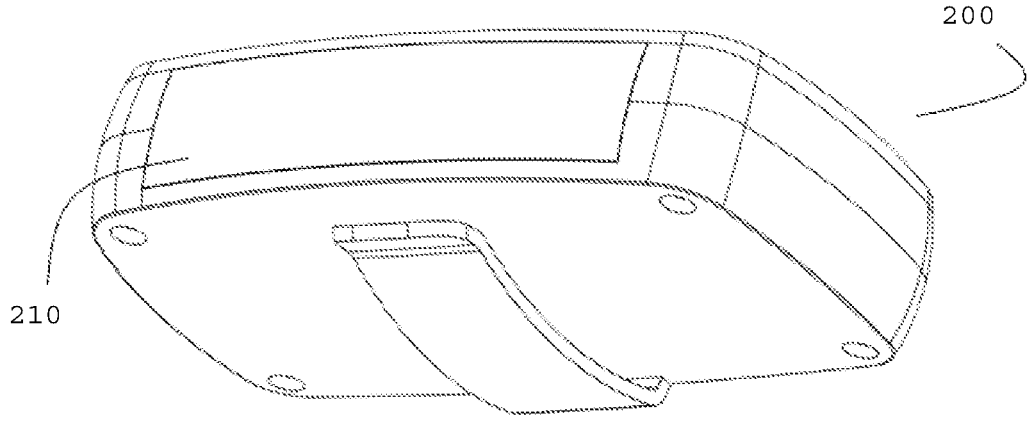
FIG. 6B shows a perspective view of an embodiment of the airtight medicine box with the inclusion of the medicine drawer.
Figure 6C:
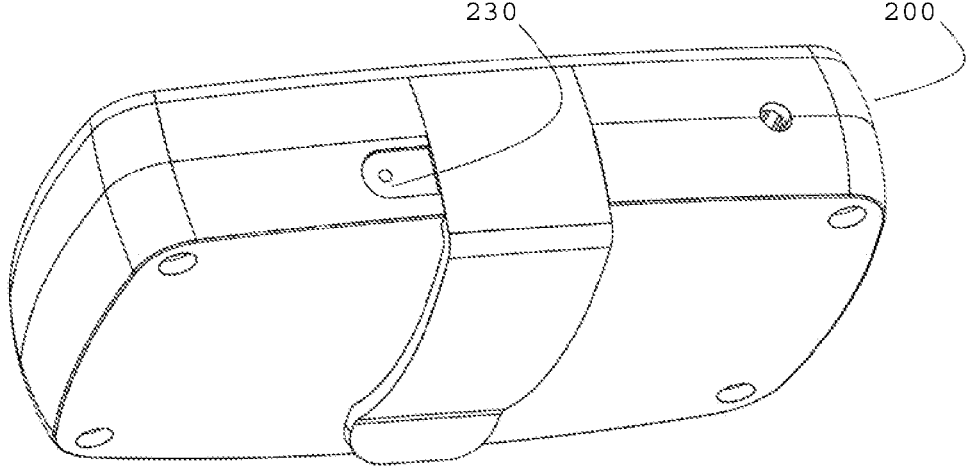
FIG. 6C shows a perspective view of an embodiment of the airtight medicine box, showing the safety lock.
Figure 7:
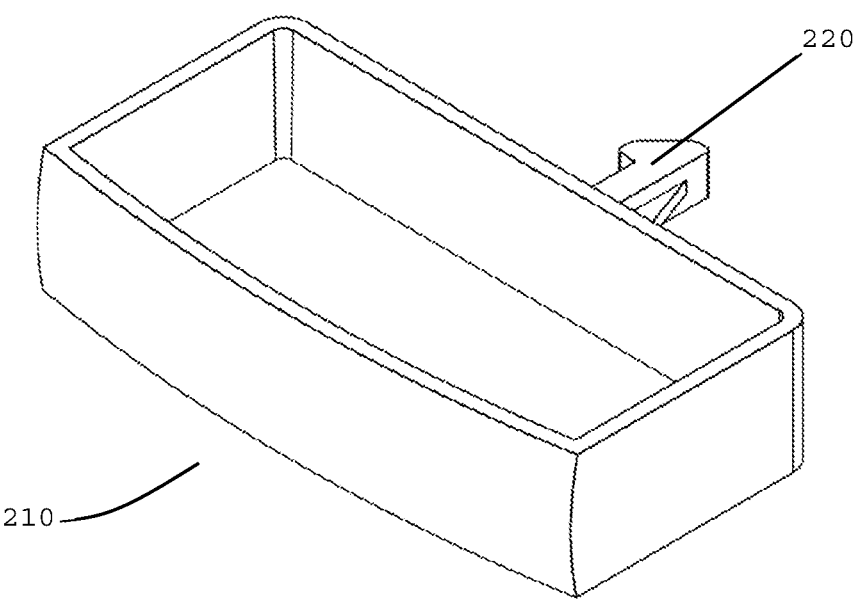
FIG. 7 shows a sectional view of the medication drawer, highlighting a lock belonging to the locking system.
Figure 8:
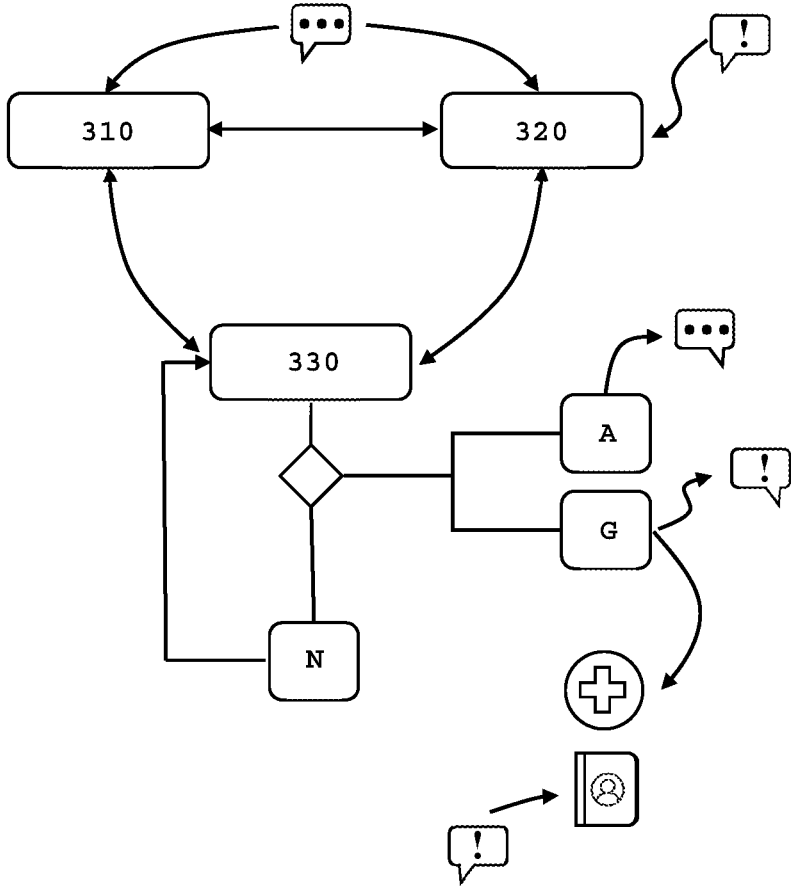
FIG. 8 is a schematic illustration of the flow of communications in the system according to an embodiment, including sending communications for the altered case (A) and sending urgent communications to the practitioner and to an emergency contact, as well as contacting a health center for the serious case (G).

Let us now refer in detail to the various embodiments of the present invention, one or more examples of which are shown in the accompanying drawings. Each example is provided by way of illustration of the present invention and is not to be construed as a limitation of this invention. For example, features shown or described insofar as they form part of one embodiment may be adopted in (or be in association with) other embodiments to produce another embodiment. It is understood that the present invention should include all such modifications and variants.

Coronary artery disease (CAD) is the leading cause of death in the world. Acute myocardial infarction (AMI) is the total occlusion of the coronary artery, the vessel that supplies the heart muscle. The best treatment option is primary angioplasty: coronary artery clearance using a balloon catheter. The earlier the opening of the coronary artery, the better the treatment result, thus reducing morbidity and mortality. The maximum optimal time between the entry of an individual into the emergency room (door), plus diagnosis and treatment is up to 90 min. The main indicator in the treatment of AMI is the "Door to Balloon Time" (D2B), which is the interval between the arrival of the patient at the emergency room and the opening of his coronary artery by primary angioplasty with a balloon catheter or stent.

There is a need for the patients to have more autonomy, information, and the possibility of using resources such as telehealth in order to obtain analysis, diagnose and even to start a treatment regardless of their location. Through constant technological advances and the facilities of computing and mobile communication, it is proposed to expand the limits of this D2B paradigm in AMI, ACS and in the approach to FAA and other cardiac arrhythmias.

All data collected and analyzed by the technology are triangulated by the monitoring center, the emergency center, and the practitioner. Through an electronic signal sent by the monitoring center, the practitioner responsible for analyzing the electrocardiographic tracing issues the report and remotely triggers, if necessary, the opening of the reservoirs with the drugs, thus starting the treatment in advance, as well as reducing the time that occurs from the initial symptom of the patient with coronary obstruction until the moment of effective and definitive treatment, which is the opening of the coronary artery by primary angioplasty. The same process can be performed considering cardiac arrhythmia such as FAA, with less than 24 to 48 hours of onset of symptoms, providing definitive treatment with the dispensing of appropriate medications by remotely opening the reservoirs with the medications as soon as the diagnosis is confirmed.

Individuals with CAD will be instructed to self-monitor with the support of telemedicine to speed up the verification of their symptoms. Therefore, the significant reduction in the time from the onset of symptoms to the opening of the coronary artery will occur through the combination of a remote monitoring network that generates reports and supports patients at risk of AMI and ACS, thus disseminating the use of the portable ECG system of the present invention. The same can happen with patients who have FAA-type arrhythmia, from the moment they feel changes in heart rhythm starting within a period of up to 48 hours.

The present invention provides a process for collecting, storing, analyzing and visualizing electrocardiographic (ECG) data collected by a portable ECG device (100) with embedded wireless communication technology, additionally containing at least one device with wireless communication technology, an airtight box (200) containing drugs and at least one central data storage system (330). Additionally, the process includes the use of a portable ECG device (100), a hermetically closed medicine box (200) containing a lock system, a first device (310) to be accessed by the patient, a second device (320) to be accessed by the practitioner, a platform for graphical display of ECG data and a central (330) for remote storage and processing of data.

The ECG device (100) performs the reading of electrocardiographic data through an electrode array (130) coupled to a mini portable ECG device (140), and transmits them to the platform through wireless communication technology, embedded on a hardware board. The electrode array (130) is formed by 4 electrodes (130) with a 3-lead reading, which can reach 15, 18 or even 22 leads, considering that there may be variations when compared to the traditional 12-lead ECG with 10 electrodes.

The hardware board and the mini-ECG device (140) are contained by a housing (110A, 110B, 110C), which additionally contains a rechargeable battery (120). The hardware board contains, in addition to wireless communication technology, a global positioning system (GPS), start button (141), a rechargeable battery charging port (120) and an equipment configuration and programming port. In some embodiments of the present invention, the battery (120) is of the Li-Ion type, containing luminous LEDs that indicate the operation of the device, also indicating the waiting of the system for connection. The application sends frequent notifications to the user to charge the battery, regardless of the load. If the battery is below 20%, messages are sent daily.

The process according to the present invention collects the electrocardiographic data and transmits them to the platform, through Wi-Fi, BLE (Bluetooth), GSM technology, 3G, 4G, 5G and, optionally, through data transmission cable. The signals captured by the ECG device (100) are treated by a data analysis suite that performs signal cleaning, amplification, and processing. The signal processing is carried out by algorithm-numerical modeling, which can be LSTM (Long Short-Term Network), UTC (Universal Transformation Coefficient), any vectorized formulation (vector-Based) or another algorithm-numerical method used in the state of art, the calculations performed being compared to the 12-lead ECG reading, which can reach 18 or even 22 leads. In one embodiment, the analysis suite is a hardware embedded on the hardware board and is composed of at least one signal amplifier, at least one high-pass filter, and at least one microprocessor, and the numerical method is automatically chosen based on the number of input ports in use (number of electrodes (130)). In one embodiment, the analysis suite is a software embedded in the first device (310) and is an integral part of the platform software for graphic display of the ECG, performing the functions of high-pass filter, signal amplifier and processing, and the numerical method is automatically chosen, based on the number of data read and transmitted (number of electrodes (130)). If 4 data are read or 4 input ports are used, the algorithm-numerical method reproduces the M additional signals, being M=8, for a 12-lead method, going up to M=18, for a 22-lead method.

Data is stored on the platform, which can be an application installed on the device (App) or an application installed in the data central (330) and accessible via the web (Web App). The platform may alternatively be accessible via the Web.

The reading process begins with the fixation of the electrodes (130) on the patient in which the data will be read, wherein the electrodes (130) are fixed directly on the skin or attached to a vest-type garment. After fixation, the ECG device (100) is started by the start button (141), electrocardiographic data are collected and processed, and the geospatial positioning of the patient is collected. Electrocardiographic data and patient positioning information are forwarded to the first device (310) in real time, via Wi-Fi, BLE, GSM, 3G, 4G, 5G technologies or a data transmission cable. Data is received by the first device (310) for storage, display and analysis by the platform accessed by the first device (310). Finally, the data that has already been treated and processed are forwarded to the central (330) for remote storage and processing of data through at least one of Wi-Fi, 3G, 4G, 5G, LAN, Ethernet, and other network connections. If the analysis suite is a hardware, the electrocardiographic data are received by the first device (310) already treated and processed, being only stored for later display and analysis by the platform. If the analysis suite is a software, the electrocardiographic data are received by the first device (310) and are processed before storage, for later display and analysis.

In one embodiment, activation of the start button (141) is performed manually by the patient, by pressing a physical button present on the ECG device (100). In one mode, the activation of the start button (141) is done remotely, through the indication of the start of reading performed by the platform, by pressing a virtual button. The remote activation can be performed by the patient himself by the first device (310), by sending an activation signal from the start button (141) of the first device (310) to the ECG device (100) through at least one of the BLE, Wi-Fi, 3G, 4G and 5G technologies. Alternatively, remote activation can be performed by the practitioner via the second device (320), through the steps of sending the start button activation signal (141) from the second device (320) to the central for remote data storage and processing (330) through at least one of Wi-Fi, 3G, 4G, 5G, LAN, Ethernet and other network connections, by issuing a signal to activate the start button (141) of the central for remote data storage and processing (330) to the first device (310) through at least one of Wi-Fi, 3G, 4G, 5G, LAN, Ethernet and other network connections, and by issuing a start button activation signal (141) of the first device (310) to the ECG device (100) via at least one of BLE, Wi-Fi, 3G, 4G and 5G technologies.

Electrocardiographic data and geospatial positioning data are received by the central (330) for remote storage and processing in real time to perform the analysis of the processed ECG data, in which the analysis considers the patient's ECG data history existing in the central (330) of storage and processing and the publicly known ECG data history, with the public knowledge history being part of the central database (330) for storage and processing, and the public knowledge history includes ECG data of heart diseases, such as valve heart disease, hypertensive heart disease, ischemic heart disease, acute coronary syndromes, acute myocardial infarction, congenital heart disease, myocardial disease, and ECG data of heart arrhythmias such as tachycardia, bradycardia, sinus node disease, atrial fibrillation, extrasystole, fascicular block, atrioventricular block, ventricular arrhythmia, hereditary arrhythmia, other arrhythmias and sudden death. In an embodiment, data is accessed by the practitioner in real time for analysis and report issuance. The analysis classifies in real time the received ECG data. The practitioner interprets the received electrocardiographic trace and selects the diagnosis in the application of his/her smartphone, by immediately sending, in real time, a notification to the application of the user (patient) who receives the report with his/her diagnosis. In case of acute myocardial infarction or arrhythmia, this notification sent by the application will automatically and remotely activate the box containing medication (200) and will dispense the medication in the appropriate dose for the specific clinical condition diagnosed by the practitioner.

In one embodiment, the analysis classifies the received ECG data as N, A or G, with data classified as N (Normal) indicating no heart disease or arrhythmia, data classified as A (Altered) indicating the existence of heart disease or arrhythmia without imminent risk of patient death or disability, and data classified as G (Severe) indicating the existence of imminent risk of patient death or disability. After analysis performed by artificial intelligence, the data storage central (330) sends the practitioner and/or the patient a notification about his/her condition. The notification is of the type previously registered by the practitioner or patient, being at least one of SMS, MMS, e-mail, application notification and telephone call.

In one embodiment, the data classified as "A" are forwarded to the practitioner and stored in the system, and a notification is forwarded to both the practitioner and the patient, and the practitioner remotely releases the lock (220) of the hermetically sealed box locking system (200) so that the patient has access to the medication dosage released by the practitioner.

In one embodiment, data classified as "G" are forwarded to the practitioner and stored in the system, and an urgent notification is forwarded to both the practitioner and the patient, and the notification contains at least the geospatial location of the patient and the heart disease or identified anomaly. An emergency medical center selected by the geospatial location of the patient is contacted automatically. An emergency notification is forwarded to at least one emergency contact pre-registered by the patient, and the emergency notification contains at least the geospatial location of the patient and the contact of the emergency medical center contacted. The practitioner remotely releases the lock (220) of the hermetically closed box locking system (200) so that the patient has access to the medication dosage released by the practitioner. In the event of the lock release electronic system (220) of the lock system, the patient performs the manual opening of the safety lock (230), being this manual opening of the mechanical drive type.

The present invention additionally provides a system for collecting, storing, analyzing, and visualizing electrocardiographic data (ECG) collected by a portable ECG device (100) with embedded wireless communication technology, additionally containing at least one device with wireless communication technology, an airtight box (200) containing medication and at least one central data storage system (330). Additionally, the system includes a portable ECG device (100), a hermetically sealed medication box (200) containing a locking system, a first device (310) to be accessed by the patient, a second device (320) to be accessed by the practitioner, a platform for graphical display of ECG data and a central for remote data storage and processing (330).

The ECG device (100) performs the reading of electrocardiographic data, through an array of 4 electrodes (130) coupled to a mini portable ECG device (140) and transmits them to the platform through wireless communication technology, embedded in a hardware board.

The mini-ECG device (140) captures the electronic signals by the electrodes (130) allowing remote monitoring of the electrocardiogram. The collected data and GPS location are transferred online to a first patient access device (310).

This system integrates hardware and software and allows the transmission of low voltage electronic signals through the internet of things to an integrated monitoring center, and creates an interface that allows shortening the time from the onset of symptoms that may be the foreshadowing of an acute coronary syndrome (ACS), or an acute myocardial infarction (AMI), or atrial fibrillation (AF), or other cardiac arrhythmia, until the definitive treatment, also being able to anticipate the beginning of the treatment, from the remote dispensation of the medicines available in the medicine box (200).

The hardware board and the mini-ECG device (140) are contained by a housing (110A, 110B, 110C), which additionally contains a rechargeable battery (120). The hardware board contains, in addition to wireless communication technology, a global positioning system (GPS), start button (141), a rechargeable battery charging port (120) and an equipment configuration and programming port. In some embodiments of the present invention, the battery (120) is of the Li-Ion type, containing LEDs that act as light indicators of operation and battery status, and a buzzer, acting as a sound indicator of battery status. In one embodiment, an electrode (130B) is positioned on the bottom cover of the ECG device (100).

In one embodiment, the electrode array (130) connects to the ECG device (100) through a conductive track. In one embodiment, the electrode array (130) sends the data collected to the ECG device (100) by means of wireless transmission.

In one embodiment, the electrode array (130) is positioned directly on the skin of the patient. In one embodiment, the electrode array (130) is coupled to a garment worn on the chest region of the patient, wherein the garment is composed of woven textile yarns of any one among polyamide, synthetic rubber, expandable fiber, natural fibers and synthetic fibers and has in its manufacturing composition a set of stainless steel wires arranged in any form such as horizontal, vertical, diagonal, square mesh, rectangular mesh, and any combination between horizontally, vertically and diagonally. Additionally, the garment has antibacterial treatment. In one embodiment, the garment is biodegradable. In one embodiment, the set of steel wires has conductivity properties of electronic signals. In one embodiment, the set of steel wires is coated with one of conductive material pastes and conductive material inks, the conductive material being any of carbon and silver.

The housing (110A, 110B, 110C) of the ECG device (100) comprises an upper cover (110A), a lower cover (110B) and an intermediate cover (110C) and, in one embodiment, an electrode (130B) of the electrode array (130) is attached to the bottom cover (110B) of the portable ECG device (100). The housing (110A, 110B, 110C) is watertight and/or immersion proof. In one embodiment, the housing (110A, 110B, 110C) has width L, with L being between 20 mm and 40 mm, height H, with H being between 8 mm and 25 mm, and length C, with C being between 40 mm and 70 mm.

In one embodiment, the intermediate cover (110C) consists of a material among silicone, natural rubber, synthetic rubber, urethane elastomer, fluorine elastomer, chloropretan, ethylene propylene, polyurethane, polytetrafluoroethylene, copolymers or any combination of silicone, natural rubber, synthetic rubber, urethane elastomer, fluorine elastomer, chloropretan, ethylene propylene, polyurethane, polytetrafluoroethylene and copolymers. Additionally, the intermediate cover (110C) can be made of any malleable material known from the state of art, natural or synthetic, this material being non-conductive and capable of providing tightness to the ECG device.

In one embodiment, the upper cover (110A) and the bottom cover (110B) are comprised of high rigidity material, any of which being made of thermoplastic polymer, thermoset polymer, high rigidity synthetic rubber, high rigidity natural rubber, polymers or copolymers, plastic and aluminum or any material, natural or synthetic, that is non-conductive.

The ECG device (100) sends frequent, weekly notifications to the first device (310), requesting the recharge of the battery (120). If the Li-Ion rechargeable battery (120) reaches 20% charge, the ECG device (100) sends a daily notification to the first device (310). In one embodiment, the ECG device (100) initiates low power mode if the Li-Ion battery (120) reaches 20% charge.

According to an embodiment of the present invention, a notification is sent to the second device (320), accessed by the practitioner, for cases of patients with heart diseases or pre-diagnostic cardiac anomalies, in which the notification informs the level of charge remaining in the battery (120) of Li-Ion, the last ECG reading and the last geospatial location of the patient.

According to an embodiment of the present invention, the ECG device (100) is adaptable to portable devices with wireless technology, by means of any one of BLE and NFC, in which the portable wireless devices are any one among a smart ring, a smart bracelet and a smart watch.

According to an embodiment of the present invention, the platform for graphical display of ECG data additionally has the functions of reading, processing, and displaying vital signs among oxygen saturation, heart rate, pulse rate, blood pressure, body temperature, vascular auscultation and respiratory auscultation, ultrasound data, and Doppler ultrasound data. Cardiac and pulmonary (respiratory) auscultations are performed using a stethoscope adapted for connection to the first device (310), having any connection port among USB type A, USB type B, USB type C, USB mini type A, USB mini type B, micro-USB type A, micro USB type B, USB 3.0 and lightning. Oxygen saturation is determined by means of at least one of pulse oximetry and finger oximetry. Ultrasound data and Doppler ultrasound data are collected by means of a mini ultrasound adapted to connect to the first device (310), having any connection port among USB type A, USB type B, USB type C, USB mini type A, USB mini type B, micro-USB type A, micro USB type B, USB 3.0 and lightning.

The device encompasses the variation of electrical potentials generated by the electrical activity of the heart. 4 channels are read, and M channels are generated by the appropriate algorithm-numerical method. For example, for the 12-lead method, 4 channels are read and 8 more are generated. The acquisition of electrical signals is started when the start button (141) is activated, either manually, by the patient or virtually, by the patient or by the practitioner, being acquired 256 points per second, during an interval of 15 seconds. 3 to 8 seconds are used to adjust the impedance of each skin type. For example, the analytics central is a hardware element. In this case, the values that are read are stored in a NOR memory, until they can be sent to the first device (310) through a wireless connection. Meanwhile, the GPS is started so that it can synchronize the satellites and identify the location of the patient, until the coordinates are received, or the time limit is exceeded.

For the acquisition of geographic coordinates data, a GPS module formed for U1 electronic circuit is used, which delivers data to the processing unit in NMEA0183 format, with latitude and longitude data. Components LED1 and LED2 are responsible for the operational signaling of the equipment and switch S1 for starting operation.

The circuit is powered by a rechargeable LI-ION battery (120) and the electronic circuit U1, dedicated front-end battery charger (120), is responsible for its management. The purpose of the electronic circuit U2 is to regulate the voltage levels to +3.3V, which is necessary for the functioning of the other electronic circuits.

Example: Analysis Suite being a Hardware Functional Description of the Circuit Biometric data (analog) are read through input connector J1, the signals pass through a high frequency filter formed by components R9, R5, R7, R11, R13, R15, R17, R19, R21, R25, R26, R22, R20, R18, R16, R14, R12, R8, R6, R23, C51, C52, C23, C24, C25, C26, C28, C29, C32, C33, C34, C35, C36, C37, C38, C3, C49, C50, C54 and C55.

Protection against electrostatic discharges at the signal input is provided by the diodes from D1 to D9, which are responsible for keeping the levels within the levels accepted by the A/D converter. Signal acquisition is performed by the U4 analog front-end, which is composed of 8 24-bit delta-sigma A/D converters. The symmetric voltage levels of +2.5 Volts and −2.5 Volts, which are necessary for matching the signal levels to the analog front-end, are generated by the electronic circuits U1, U2 and U3.

Data storage is carried out by electronic circuit U3, non-volatile memory, responsible for recording the acquired data for later transmission. Circuit U8 is composed of a solid-state switch responsible for activating the electromagnet to release the drawer (210) for medications, according to the application request. The USB input includes protection against surges and electrostatic discharges, formed by the U7 circuit, solid state TVS protector.

Wireless communication is performed by electronic circuit U6, responsible for sending data to the FTP server. Circuit U5 is composed of a solid-state switch, responsible for turning off the electronic circuit U6 when it is not in operation.

In one embodiment, the electronic circuit U6 is a Quad-Band GSM modem, and the connector J6 is the receptacle for the SIMCARD GSM that has its protection against electrostatic surges performed by the electronic circuit TVS1. The electronic circuit U4, microcontroller of the ARM family, responsible for executing the application software, is also responsible for data processing and treatment.

The platform accessed by the first device (310) adds data, time, and geospatial positioning, and submits the exam to the FTP server. It is possible to view both the recorded exam and real-time monitoring of cardiac signals. If the file is not successfully sent, an error log is stored and a retry is performed after a period between 2 and 10 seconds. This process will be repeated until the exam is successfully submitted to the server. The log is sent to the central (330) along with the next valid exam.

The present invention, among all the technological benefits described above, contributes to the immediate diagnosis of symptoms in ACS, AMI, FAA and other cardiac arrhythmias and allows to drastically reduce the time between the onset of symptoms and the primary angioplasty, definitive treatment of AMI, early initiation of treatment in ACS and AMI, and definitive treatment of AAF and other cardiac arrhythmias, through proper administration of the drug dose contained in the drug compartment (210). The medical and hospital network will have access to the SMI to update data, register new care teams and obtain information from patients who are submitted to their appointments.

In the claims presented in this document, the sole purpose of the references in parentheses is to facilitate reading: they cannot be considered as restrictive factors regarding the field of protection claimed in the specific claims.

The invention claimed is:

1. Process for collecting, storing, analyzing and visualizing electrocardiographic (ECG) data collected by a portable ECG device (100) with embedded wireless communication technology, additionally containing at least one device with wireless communication technology, an airtight box (200) comprising medicines and at least one central data storage system (330), wherein it comprises a portable ECG device (100), comprising
   one electrode array (130),
   a housing (110A, 110B, 110c),
   a rechargeable battery (120) contained by the housing (110A, 110B, 110C), and
   a portable mini-ECG apparatus (140) contained by the housing (110A, 110B, 110C), with a hardware board with embedded wireless communication technology, a global positioning system (GPS), a start button (141), a rechargeable battery charging port (120) and an equipment configuration and programming port;
a hermetically sealed box (200) of medicines containing a locking system;
a first device (310), accessed by a patient;
a second device (320), accessed by a doctor or expert;
a platform for graphical display of ECG data, wherein
   the platform is accessed by the first device (310) in the form of at least one between an application, a website, and a web application (Web App), and
   the platform is accessed by the second device (320) in the form of at least one between an application, a website, and a web application (Web App); and a central (330) for remote data storage and processing.

2. The process according to claim 1, wherein it comprises an electrocardiographic signal analysis suite embedded in the hardware board, consisting of
   at least one signal amplifier,
   at least one high-pass filter, and
   at least one microprocessor,
wherein the signal analysis set receives signals captured by the electrodes (130) and generates M signals through an algorithmic-numerical modeling,
   the algorithm-numerical modeling being any one of LSTM (Long Short-Term Network), UTC (Universal Transformation Coefficient) and vectorized (Vector-Based) formulations, and
   the M signals are generated according to a 12-lead ECG comparison (M=8), reaching up to 22 leads (M=18).

3. The process according to claim 1, wherein it comprises one electrocardiographic signal analysis set that is embedded in the first device (310), wherein
   the electrocardiographic signal analysis suite is an integral part of the platform software for graphical display of the ECG, and it performs the functions of high-pass filter, signal amplifier and processing,
   the signal analysis suite receives the signals captured by the electrodes (130) and generates M signals by means of the algorithmic-numerical modeling,
   the algorithm-numerical modeling being any one of LSTM (Long Short-Term Network), UTC (Universal Transformation Coefficient) and vectorized (Vector-Based) formulations, and
   the M signals are generated according to a 12-lead ECG comparison (M=8), which can reach 22 leads (M=18); and
   the platform is accessed by the first device (310) in the form of at least one between an application (App) and a web application (Web App).

4. The process according to claim 1, wherein it comprises the steps of
   attaching the electrode array (130) to the patient;
   activating the ECG device (100) with the start button (141);
   collection and processing of electrocardiographic signals by the ECG device (100);
   collection of a geospatial positioning data by the GPS;
   sending a data (D2) containing the processed signals and geospatial position to the first device (310) through at least one of BLE, Wi-Fi, 3G, 4G and 5G, in real time;
   receiving the data (D2) by the first device (310) for storage, display and analysis by the platform accessed by the first device (310); and
   sending the data (D2) to the remote data storage and processing central (330) through at least one of Wi-Fi, 3G, 4G, 5G, LAN, Ethernet, and other network connections.

5. The process according to claim 1, wherein it comprises the steps of
   attaching the electrode array (130) to the patient;
   activating the ECG device (100) with the start button (141);
   collection of electrocardiographic signals by the ECG device (100);
   collection of a geospatial positioning data by the GPS;
   sending a data (D1) containing the electrocardiographic signals and geospatial position to the first device (310) through at least one of BLE, Wi-Fi, 3G, 4G and 5G, in real time;

receiving the data (D1) by the first device (310) for storage, display and analysis by the platform accessed by the first device (310);

processing the electrocardiographic signals contained in the data (D1) received by the first device (310); and sending a processed data (D2) to the central (330) for remote data storage and processing through at least one of Wi-Fi, 3G, 4G, 5G, LAN, Ethernet, and other network connections.

6. The process according to the claim 5, wherein it comprises an electrode (130*b*) of the electrode array (130) that is attached to the bottom cover (110*b*) of the portable ECG device (100).

7. The process according to claim 1, wherein the activation of the start button (141) is performed manually by the patient; or remotely by the patient by sending a start button activation signal (141) from the first device (310) to the ECG device (100) through at least one of BLE, Wi-Fi, 3G, 4G and 5G; or remotely by the doctor or expert through the steps of sending a start button activation signal (141) from the second device (320) to the remote data storage and processing central (330) through at least one of Wi-Fi, 3G, 4G, 5G, LAN, Ethernet and other network connections;

sending a start button activation signal (141) from the remote data storage and processing central (330) to the first device (310) through at least one of Wi-Fi, 3G, 4G, 5G, LAN, Ethernet, and other network connections; and sending a start button activation signal (141) from the first device (310) to the ECG device (100) through at least one of BLE, Wi-Fi, 3G, 4G and 5G.

8. The process according to claim 1, wherein the remote data storage and processing central (330) analyzes the processed ECG data received in real time, wherein the analysis considers a ECG data history from the patient that is present in the storage and processing central (330); and a historical ECG data of public knowledge, considering that the publicly known history is part of the database (330) from the storage and processing central, and the public knowledge history includes ECG data from heart diseases, such as valve heart disease, hypertensive heart disease, ischemic heart disease, congenital heart disease, myocardial diseases, coronary artery disease, acute coronary syndromes, acute myocardial infarction, and ECG data from arrhythmias of the heart, such as tachycardia, bradycardia, sinus node disease, atrial fibrillation, extrasystole, fascicular block, atrioventricular block, ventricular arrhythmia, hereditary arrhythmia, and sudden death.

9. The process according to claim 1, wherein the analysis classifies the received ECG data, in real time, in which data are classified by the doctor or expert after analyzing the ECG signals;

the doctor or expert issues a report with his medical opinion of an ECG result; and a notification is forwarded to the patient, through the first device (310), informing a receipt of the report.

10. The process according to claim 1, wherein the doctor or expert analyzes the processed ECG data received after completion of reading, wherein the analysis considers symptoms indicated by the patient at the beginning of an ECG exam.

11. The process according to claim 10, wherein the storage and processing central (330) forwards an emergency notification to both the doctor or expert and the patient in case of a report indicating risk of death, of permanent or of intermittent damage to the patient, in which the emergency notification is forwarded to the doctor or expert, and the notification is forwarded through one between an in-app notification and a push notification, and the notification contains at least the geospatial location of the patient and the identified heart disease or anomaly;

the emergency notification is forwarded to the patient through a medium between in-app notification and push notification;

an emergency medical center is automatically contacted, in which the medical center is selected by the geospatial location of the patient; and the emergency notification is forwarded to at least one emergency contact pre-registered by the patient, in which the emergency notification contains at least the geospatial location of the patient and the contact of the contacted emergency medical center.

12. The process according to claim 1, wherein the analysis classifies a received ECG data in real time, in which data are classified by the doctor or expert after analyzing the ECG signals;

the doctor or expert issues a report with his medical opinion of an ECG result;

a notification is forwarded to the patient, through the first device (310), informing a receipt of the report and notifying a dosage of a medication to be taken by the patient; and the doctor or expert remotely releases an opening of the hermetically closed box (200).

13. The process according to claim 12, wherein the doctor or expert remotely releases a locking system of the hermetically sealed box (200) so that the patient has access to a drug dosage that is specific to his/her condition diagnosed by the system.

* * * * *